Figure 1:
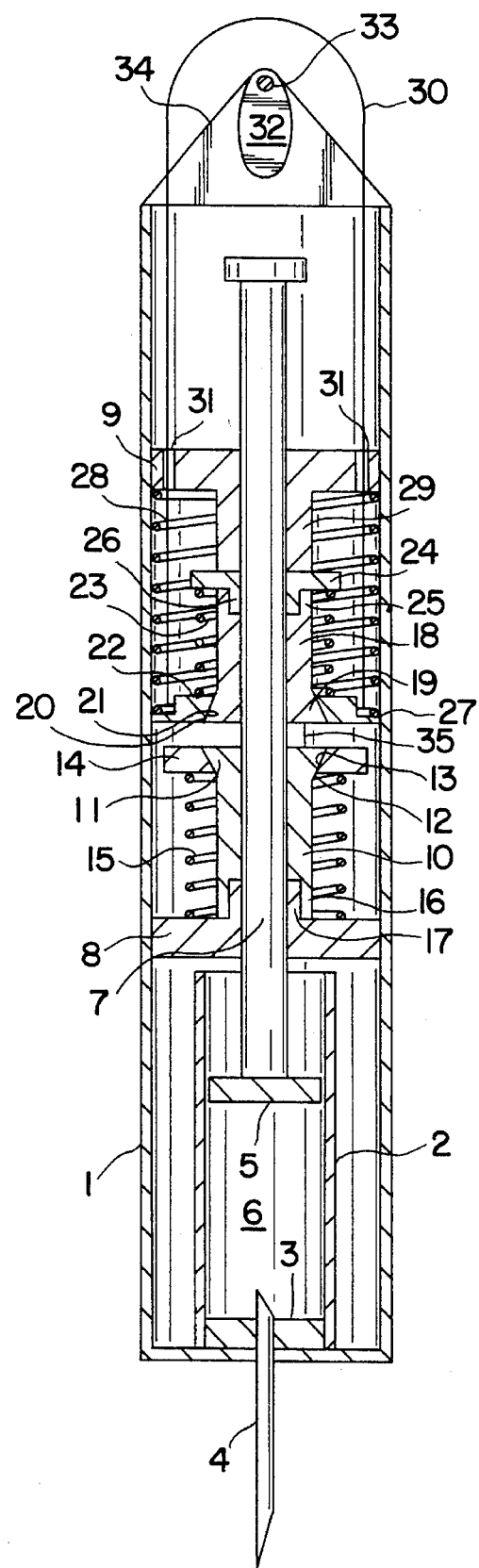

United States Patent [19]

Fryklund et al.

[11] Patent Number: 5,545,144
[45] Date of Patent: Aug. 13, 1996

[54] METHOD AND DEVICE FOR DOSING A LIQUID PREPARATION

[75] Inventors: Linda Fryklund, Sollentune; Birger Hjertman, Vällingby; Marie-Louise Gustavsson, Stockholm; Jacob Kaluski, SaltsjöBoo; Gustav Levander, Bromma; Olle Ljungquist, Täby; Anders Ström, Enskede; Jonas Virding, Lidingö, all of Sweden

[73] Assignee: Pharmacia AB, Sweden

[21] Appl. No.: 232,109

[22] PCT Filed: Sep. 23, 1992

[86] PCT No.: PCT/SE92/00654

§ 371 Date: Sep. 26, 1994

§ 102(e) Date: Sep. 26, 1994

[87] PCT Pub. No.: WO93/08854

PCT Pub. Date: May 13, 1993

[30] Foreign Application Priority Data

Nov. 1, 1991 [SE] Sweden ................... 9103215

[51] Int. Cl.⁶ ........................ A61M 5/00
[52] U.S. Cl. ............ 604/187; 604/186; 604/135
[58] Field of Search ................ 604/232, 207, 604/86, 82, 208, 209, 135, 191; 222/137, 309, 145.7

[56] References Cited

U.S. PATENT DOCUMENTS

| | | |
|---|---|---|
| 3,934,585 | 1/1976 | Manrice . |
| 4,284,077 | 8/1981 | Wagner . |
| 4,561,856 | 12/1985 | Cochran . |
| 4,564,360 | 1/1986 | Young et al. . |
| 4,659,327 | 4/1987 | Bennett et al. . |
| 5,423,752 | 6/1995 | Haber et al. . |

FOREIGN PATENT DOCUMENTS

| | | |
|---|---|---|
| 0450905A1 | 4/1991 | European Pat. Off. . |
| 0378305A1 | 7/1991 | European Pat. Off. . |
| 161600 | 4/1973 | New Zealand . |
| 168244 | 9/1975 | New Zealand . |
| WO88/07874 | 10/1988 | New Zealand . |
| 227895 | 3/1991 | New Zealand . |
| 1230522 | 5/1971 | United Kingdom . |
| WO82/02662 | 8/1982 | WIPO . |
| WO91/14467 | 10/1991 | WIPO . |

*Primary Examiner*—Randall L. Green
*Assistant Examiner*—Perry E. Van Over
*Attorney, Agent, or Firm*—Pollock, Vande Sande & Priddy

[57] ABSTRACT

A liquid preparation of a pharmaceutically active agent having a defined composition is repeatedly dosed from a multi-dose container having a defined volume. The amount dosed is selected as 1/N of the volume of the multi-dose container, N being an integer having a value of 2 or higher.

A device for dosing a liquid preparation comprises a holder (1) for a multi-dose container (2), which has a movable rear wall (5) acting as a piston for expelling the liquid preparation (6) from the container, and a piston rod (7), which is provided with releasable blocking means (11, 14, 19, 22), such that the movement of the piston rod is limited to a preset length (35) corresponding to an expelled volume of 1/N of the volume of said multi-dose container, N being an integer having a value of 2 or higher.

A preferred embodiment of the device is as an injection device for repeated parenteral injections from an injection cartridge.

16 Claims, 2 Drawing Sheets

METHOD AND DEVICE FOR DOSING A LIQUID PREPARATION

The present invention is directed to the dosing of liquid preparations. More specifically, the invention refers to a method and a system for the repeated dosing of liquid pharmaceutical preparations which are to be administered. Still more specifically, the invention refers to a method and a system for the repeated dosing and administering of liquid pharmaceutical preparations by parenteral injection from a multi-dose container. Furthermore, the invention also refers to a device for carrying out the method of the invention, especially then in the form of an injection device for repeatedly administering parenteral injections from an injection cartridge.

When a pharmaceutical agent is prescribed by a physician, the amount or dose to be administered to the patient is usually expressed in well-known units, such as milliliters or international units (IU). The dose is determined by such factors as the health status and weight of the patient, for example, and by rules from the health authorities. In those cases where the patient himself is to administer the doses, the physician then selects a suitable multi-dose container, from which a number of doses may be administered. Such a multi-dose container may be a vial, from which each individual dose is withdrawn by means of a hypodermic syringe, or it may be in the form of an injection cartridge, which is to be inserted in an injection device for repeated administrations. Injection cartridges have found a wide use because of the easiness in their handling and the diminished risk of infections, especially when the patient has to give himself repeated administrations. Injection devices in the shape of a pen for repeated injections of such preparations as, for example, insulin and growth hormones are commercially available. The user inserts an injection cartridge in the device and attaches an injection needle to the cartridge, and the device is then ready for repeated injections. The device may be set at different doses and is usually graduated in such units as milliliters or International Units.

It is usually desirable that the dose is set in such a way that there will be a minimum residue of the preparation in the multi-dose container after a series of injections have been administered. This is of special importance when very expensive preparations are administered, such as growth hormones. This is not a problem when the multi-dose container is a vial from which the individual doses are withdrawn. If the remaining amount of preparation in the vial is insufficient for a complete dose, the user simply takes the missing amount from a fresh vial, and there will be no unused residue.

However, this is not possible when an injection cartridge is used in an injection device of a known type, and depending on the relation between the prescribed dose and the contents of the cartridge, the residue may be considerable. For instance, for a cartridge containing 12 I.U. of a preparation, only the doses of 1, 2, 3, 4, 6, and 12 I.U. will leave no residue, but for other doses, there will be a considerable waste. Thus, for example, a dose of 4.5 I.U. will give a residue of 3 I.U. after two administrations, and a dose of 8 I.U. will give a residue of 4 I.U. after one administration. A dose of 6.25 I.U. will give a residue of 5.75 I.U. after one administration, that is, nearly half of the contents of the cartridge. For very expensive preparations, such as growth hormones, this is quite unacceptable.

It is not suitable for the user to give himself two injections to administer the prescribed dose, as this will mean that a new dose value has to be set for the first injection from the second cartridge, and the prescribed dose value then reset. This may easily lead to errors in the calculation and setting of the doses.

For expensive preparations, special dosage schemes have been tried, where the dose is varied from each administration to the subsequent one. This complicates the prescription for the physician, and may also lead to errors. Furthermore, this means that only the average dose will be correct, and deviations will occur at each individual administration. This may lead to side effects.

By the method and the device of the invention, these disadvantages are eliminated. According to the present invention, a liquid preparation of a pharmaceutically active agent is dosed by repeated administrations from a multi-dose container having a defined volume, in such a way that the amount dosed is an integer fraction of the volume of the multi-dose container. Expressed in another way, the amount dosed is selected as 1/N of the volume of the multi-dose container, N being an integer having the value of 2 or higher. The concentration of the preparation in the multi-dose container is adapted to provide the desired dose.

The value of N is selected and set before the preparation is withdrawn from the multi-dose container, and is then maintained unchanged through N successive injections, when said multi-dose container has been emptied.

In a more preferred embodiment, the dosing is a series of N successive parenteral injections from an injection cartridge.

To provide a suitable selection of doses to be administered by the method of the invention, a series of multi-dose containers which contain preparations of different concentrations are provided. This will give a wide range of combinations corresponding to varying doses. For instance, if four multi-dose containers with the concentrations A, B, C and D are used in an injection device wherein the contents of the container can be divided into two, three and four equal parts, the following combinations are possible:

|         | A   | B   | C   | D   |
| ------- | --- | --- | --- | --- |
| 2 parts | A/2 | B/2 | C/2 | D/2 |
| 3 parts | A/3 | B/3 | C/3 | D/3 |
| 4 parts | A/4 | B/4 | C/4 | D/4 |

It is clear that with a greater number of denominators and concentrations, the number of possible combinations becomes very great.

The greatest denominator (value of N) is determined by the number of days that the preparation can be stored, and by the number of doses per day. In one embodiment, wherein a growth hormone is administered, the maximum value of N is 21, when one dose is administered per day, and 42, when two doses are administered per day.

The smallest value of N is two, as this is the lowest value where a multi-dose container still exists. An N value of one means that the whole contents of the injection cartridge is administered, and in this case, the method of the invention is of no interest.

The invention further refers to a device for repeated dosing of a liquid preparation, comprising a holder device for a multi-dose container which has a defined volume and which contains a preparation having a defined composition. The multi-dose container is provided with a front wall which is fixed and through which may be arranged an outlet for the preparation, and a movable rear wall, which may act as a piston to expel the preparation through the outlet. In the holder device is also arranged a piston rod, by the action of which the rear movable wall may be urged forward. What characterizes the device of the invention is that the piston rod is provided with releasable blocking means, by which the forward movement of said piston rod is limited to preset defined length, which corresponds to a forward movement of the movable rear wall for a length corresponding to 1/N of the volume of the multi-dose container, N being an integer having a value of 2 or higher.

In a preferred embodiment of the device of the invention, the blocking means, after the piston rod and the rear movable wall have been moved forwards for the defined length, may be released from said piston rod and again be attached to it in such a position that the piston rod and the rear movable wall may again be moved forwards for the same defined length, and this process may be successively repeated until the piston rod and the rear movable wall have been moved forwards N times, so that the multi-dose container is empty.

In a still further preferred embodiment, the device of the invention is arranged as an injection device for repeated parenteral injections from an injection cartridge.

Figure 2:
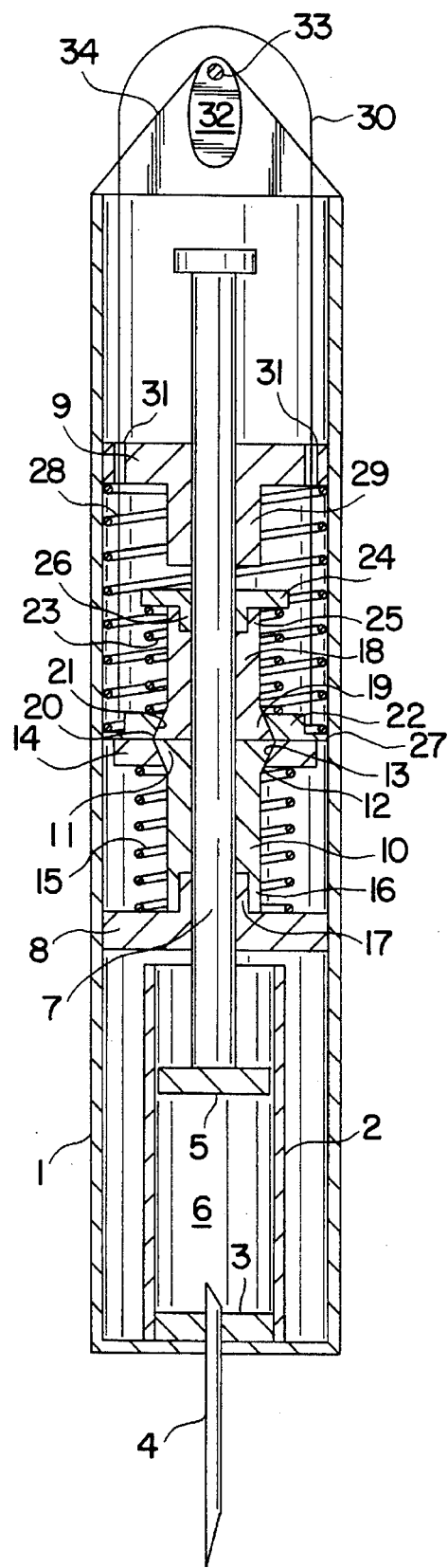

In the drawings, an example of a preferred embodiment of a device according to the invention is shown. FIG. 1 shows the device before an injection has been administered, and FIG. 2 shows the device after an injection has been administered.

When a dose of a pharmaceutical preparation is to be set and subsequently administered, the following steps are carried out.

1) The physician selects a suitable dose level against the background of the indication and the health status of the patient, directives from the health authorities and similar criteria.

2) The physician determines the weight of the patient, and with the aid of a table, a computer program, a nomogram or similar device determines the individual dose corresponding to the general dose level determined under step 1. Here, the physician will find information about which concentration of the preparation and which division of the multi-dose injection cartridge are to be used in each specific case. It is to be noted that only one approximation has to be made, namely between the actual weight of the patient and the weight given in the table.

3) The injection device is set to the division of the multi-dose cartridge (the value of N) that is to be used. This setting may be carried out by the physician, by the pharmacist where the injection device is bought, or by the patient himself on instructions from the physician. The setting cannot then be changed easily. For the setting, the device may be made adjustable, or a device may be used, in which the setting is fixed by the manufacturer of the device. In the latter case, a series of devices which are set to fixed values of N are provided, and the physician or user selects one having a suitable setting.

4) When a dose is to be administered, the patient activates the blocking means of the injection device, such that the piston rod and the rear movable wall of the multi-dose injection cartridge may be moved forward for the preset length and a defined fraction of the contents of the cartridge will be expelled and administered. When the next dose is to be administered, the blocking means are released and activated anew corresponding to the preset division of the injection cartridge. When the preset number of doses have been administered, the cartridge is empty and may be exchanged for a fresh one, the initial setting still being maintained.

The method and device of the present invention are intended for the dosing of liquid preparations of pharmaceutically active agents. The expression "liquid" is here to be given a wide interpretation, and includes liquids of varying viscosities up to high viscosity values. The liquid preparations may also be aqueous or non-aqueous solutions, emulsions or suspensions.

The method and device of the invention should not be confused with the prior art methods and devices for dosing and administering liquid preparations. The prior art devices for repeated administration from a multi-dose cartridge usually consist of an injection device which comprises a mechanism for a stepwise movement forward of the rear movable wall of the injection cartridge, such as a screw or ratchet mechanism. The steps which are possible with this type of mechanism are fixed and a dose can only be determined by a given number of steps. Thus, the mechanism may be adapted to the injection cartridge in such a manner that an advancement of the mechanism with one step will give a dosed amount of, for example, ⅛ of the volume of the cartridge. However, the mechanism cannot then be easily adapted to give a dose of, for example, 1/7, 1/9 or 1/10 of the volume of the cartridge. This means that only a limited number of dose amounts are possible without giving a residue.

In contrast to this, the dosing mechanism of the device of the invention will always give a dose which is 1/N of the volume of the cartridge, wherein N is an integer. The value of N is selected and set on the device before the series of administrations is started, and it cannot then be easily changed. This means that when the set number of N administrations have been carried out, there will be no residue remaining in the cartridge. By providing a suitable range of cartridges with varying concentrations of the preparation and a suitable range of values for N, it is possible to obtain a wide range of different doses. This range of doses may then be presented in a table, from a computer memory, or in a nomogram, for easy reference by the physician.

An embodiment of the device of the invention is shown schematically in the drawing. In this embodiment, the device is an injection device for setting and repeated administering of measured doses of a preparation by parenteral injections.

FIG. 1 shows a schematic sectional view of the device immediately before an injection is to be administered. FIG. 2 shows the device after an injection has been administered. In the figures, like parts have the same reference numbers.

The device comprises a barrel 1, which at its front end is arranged to receive an injection cartridge 2. The injection cartridge 2 has a front fixed wall 3 wherein is arranged an injection cannula or needle 4, and a rear movable wall 5, which acts as a piston, and is filled with an injectable preparation 6. The injection cartridge and its arrangement in the front end of the device are conventional, and need not be described here in more detail.

The rear movable wall 5 of the injection cartridge 2 is actuated by the piston rod 7, the front end of which is resting against the rear face of said movable wall 5. The piston rod is guided slidably through coaxial openings in the transversal walls 8 and 9. These transversal walls are solidly attached to the barrel 1, but at least one of these walls should be displaceable for setting the dose, as will be described below.

Inside the barrel 1 and between the two transversal walls 8 and 9 are arranged the releasable blocking means for the piston rod 7. These consist of a fixed front chuck 10 with jaws 11, which clamp around the piston rod 7. The jaws are provided with inclined surfaces 12 around their outer circumference, and these inclined surfaces cooperate with correspondingly inclined surfaces 13 at the inner circumference of a locking ring 14, which is urged rearward by the action of a spring 15. The chuck 10 is secured to the front transversal wall by means of the cooperating sleeves 16 and 17, and the spring 15 is arranged under compressive tension between the rear face of the transversal wall 8 and the front face of the locking ring 14. Thus, the inclined surfaces 13 of the locking ring 14 are urged rearward against the inclined surfaces 12 of the jaws 11 of the chuck 10, so that the jaws 11 are closed and will grip the piston rod 7 securely. The grip may be released by moving the locking ring 14 forward against the action of the spring 15.

The releasable blocking means further comprise a movable rear chuck 18, which is arranged to the rear of the front chuck 10. This rear chuck is of a similar construction as the front chuck 10, and has jaws 19, which are provided with external inclined surfaces 20, which cooperate with correspondingly inclined internal surfaces 21 in a rear locking ring 22. This locking ring is urged forward by the spring 23. At its rear end, the chuck 18 is solidly attached to a circular washer 24 by means of the cooperating sleeves 25 and 26. The spring 23 is arranged under compressive tension between the rear face of the locking ring 22 and the front face of the washer 24, such that the locking ring 22 will be urged forward and, through the cooperation between the inclined surfaces 20 and 21, the jaws 19 of the rear chuck 18 will be closed around the piston rod 7 and grip it securely. This grip may be released by moving the locking ring 22 rearward against the pressure of the spring 23.

The locking ring 22 is provided with a peripheral flange 27, and a spring 28 is arranged between the rear face of the flange 27 and the front face of the rear transversal wall 9, such that the spring 28 strives to urge the locking ring 22 forward. As the jaws 19 of the rear chuck 18 are closed around the piston rod 7, however, and furthermore, the jaws 11 of the front chuck 10 are also closed around the piston rod, the locking ring 22 cannot be moved forward.

A yoke 30 is attached to the locking ring 22 at its edge rearward of the flange 27, and the arms of the yoke pass through holes 31 and may be pulled rearwards against the pressure of the springs 23 and 28, and will then move the locking ring 22 rearward, so that the grip of the piston rod 7 by the jaws 19 of the chuck 18 will be released. The movement of the yoke 30 is controlled by the rotation of the cam 32 around the shaft 33. This shaft 33 is mounted between two brackets 34, which are integral with the barrel 1 of the injection device. The cam 32 may be rotated by means of a handwheel or knob (not shown), which is attached to the shaft 33.

In the position shown in FIG. 1, the device is ready for an administration of an injection. The rear face of the washer 24 rests against the front face of the sleeve 29 of the rear transversal wall 9, and there is a spacing 35 between the rear faces of the locking ring 14 and the front chuck 10 and the front faces of the locking ring 22 and the rear chuck 18. It is this spacing 35 which determines the magnitude of the dose to be administered.

FIG. 2 shows the device of the invention after an injection has been administered. The rear chuck 18 with its locking ring 22 and the washer 24 have now been moved forward by the action of the spring 28, so that the front faces of the chuck 18 and its locking ring 22 rest against the rear faces of the front chuck 10 and its locking ring 14. In its movement forward, the rear chuck has also gripped the piston rod 7 and brought it forward and in its turn moved the rear movable wall 5 of the injection cartridge 2 forward, to expel a dosed amount of the preparation 6 through the needle 4.

There is now a spacing between the rear face of the washer 24 and the front face of the sleeve 29, and this spacing is of the same magnitude as the spacing 35 shown in FIG. 1.

The function of the device of the invention is as follows:

As stated previously, FIG. 1 shows the device ready for the administering of an injection. The front chuck 10 grips the piston rod 7 by means of the locking ring 14, which is urged rearward by the action of the spring 15.

When the injection is to be administered, the front locking ring 14 is moved forward a short distance sufficient to release the grip of the piston rod 7 by the jaws 11 of the chuck 10. This may be achieved by means of, for example, an operating arm extending into the device through an opening in the barrel 1 (not shown). Other embodiments of this function are apparent to those skilled in the art.

When the grip of the piston rod 7 by the front chuck 10 is released, the piston rod will be moved forward by the action of the spring 28 on the flange 27 of the rear locking ring 22. As the jaws 19 of the rear chuck 18 are held closed around the piston rod 7 by the action of the spring 23 on the rear locking ring 22, this whole assembly will be moved forward by the spring 28, until the front face of the rear chuck 18 will abut the rear face of the front chuck 10. By this action, the piston rod 7 will move the rear movable wall 5 of the injection cartridge 2 forward for a determined distance corresponding to the spacing 35, such that a determined dose of the preparation 6 is expelled from the cartridge 2 through the needle 4.

The yoke 30 will follow the rear locking ring 22 on its forward movement, and will not be hindered by the cam 32, as this cam is pointing forwards.

After the dose has been administered, the parts of the device are in the positions shown in FIG. 2.

When a new dose is to be set for administration, the cam 32 is turned around its shaft 33 by means of a suitable handwheel or knob, which is not shown. The movement of the cam 32 will then actuate the yoke 30 to move it rearwards. This rearward movement will then also move the rear locking ring 22 rearwards, such that the jaws 19 of the rear chuck 18 are released around the piston rod 7. By the action of the spring 23 on the front face of the washer 24, which is solidly connected with the rear chuck 18, the whole assembly of washer 24, rear chuck 18, spring 23 and rear locking ring 22 will be moved rearwards until the rear face of the washer 24 abuts the front face of the sleeve 29 of the rear transversal wall 9. During this rearward movement, the piston rod 7 is kept stationary by the clamping action of the front chuck 10.

When the rear chuck 18 and the washer 24 have been moved the full distance rearwards, there is again a spacing 35 between the front faces of the rear chuck 18 and its locking ring 22 and the rear faces of the front chuck 10 and its locking ring 14. This spacing 35 corresponds to the dose set.

When the cam 32 has been rotated half a revolution, such that it is pointing rearwards and the yoke 30 is in its most rearward position, this position corresponds to a position of the rear locking ring 22 that is somewhat further rearwards than what corresponds to the washer 24 abutting against the front face of the sleeve 29. On further turning of the cam 32, the yoke 30 and the rear locking ring 22 will be moved somewhat forward by the action of the spring 23, so that the jaws 19 of the rear chuck 18 will lock securely around the piston rod 7 in its new position.

During this rearward movement, the spring 28 has also been cocked, and is ready to deliver a new injection. This feature gives the device auto-injecting properties, and there is no need for the user to exert any force for expelling the set dose of the injectable preparation 6 from the injection cartridge 2 through the needle 4.

The device is now as shown in FIG. 1, and is ready to administer a new dose. These setting and administering steps are repeated according to the injections prescribed by the physician until the injection cartridge has been emptied. The cartridge may then be removed and a fresh cartridge inserted.

In the embodiment of the device shown in the figures, the front chuck 10 is fixed to the transversal wall 8, while the rear chuck 18 is movable forwards and rearwards for the administering of a dose and the setting of a new dose for administration. However, it is also possible to arrange the fixed chuck to the rear of the movable chuck. The barrel 1 will then be provided with stopping means extending from its internal wall for stopping the forward movement of the movable chuck after a predetermined distance. The modifications necessary for this embodiment are within the competence of a person skilled in the art.

Before a fresh cartridge is inserted, the piston rod 7 should be moved back to its rearmost starting position. This may be achieved by releasing both chucks 10 and 18, and this may be arranged by inserting a suitable tool (not shown) through an opening in the wall of the barrel 1, such that the two locking rings 14 and 22 are moved forwards and rearwards, respectively, to release their grip around the jaws 11 and 19, respectively. The fresh cartridge may then be inserted, for instance by unscrewing a front portion of the barrel 1 from a rear portion thereof, so that the compartment for the cartridge becomes accessible.

The device of the invention is suitable for single-chamber as well as dual-chamber injection cartridges. Such cartridges are of a conventional character, and their design and readying for use need not be described here in more detail.

When the piston rod 7 has been moved back to its rearmost starting position, its front end should still protrude from the front transversal wall 8 for a given distance. When a single-chamber cartridge is used, this distance should be such that the front end of the piston rod will rest against the rear movable wall 5 of the injection cartridge when said cartridge has been put in its correct position and the injection device has been assembled and readied for use, such as by screwing the front and rear parts of the barrel 1 together. When a dual-chamber injection cartridge is used, the protruding length of the piston rod 7 should be such that when the cartridge has been put in its position and the device is screwed together, the front end of the piston rod 7 will push the rear movable wall 5 of the cartridge forward, such that the two components in the two chambers of the cartridge will be combined and mixed in the conventional way during the assembly of the device. The appropriate length of the piston rod 7 can easily be determined by a person skilled in the art.

The magnitude of the dose set to be administered is determined by the spacing 35 between the two locking rings 14 and 22 or between the washer 24 and the front face of the sleeve 29 of the rear transversal wall 9. This spacing 35 may be set by varying the distance between the front and rear transversal walls 8 and 9. Thus, at least one of these transversal walls 8 and 9 should be arranged to be displaced for a set distance, and it is preferred that the rear transversal wall 9 is movable, as this will not change the distance that the piston rod 7 will protrude from the front transversal wall 8 when said piston rod is in its starting position. The setting of the distance between the two transversal walls 8 and 9 may be carried out by the physician or the pharmacist by means of special tools, and this setting should then not be easily changed afterwards. In this way, it is assured that the patient will always get the same, predetermined dose.

As has been stated in the foregoing, it is an essential feature of the invention that the dose set is always 1/N of the volume of the injection cartridge, N being an integer having a value of 2 or higher. In this way, it is assured that there will be no residue of the injectable preparation when the determined number of doses have been administered. As the injection cartridge is cylindrical, a set dose will be represented as a determined distance of movement for the rear movable wall 5 of the cartridge, and the correct setting may be made with the help of a suitable scale, or the like.

The injection device of the invention shown above is especially adapted to the process of the invention, as the setting of the dose to be administered can be made continuous and not stepwise, as in the prior art processes and devices. In combination with a range of different concentrations of an injectable preparation in different injection cartridges, it has thus become possible to provide an injection system which gives the correct dose of preparation to the patient and at the same time does not leave a residue of the preparation, so that costly waste of the preparation is eliminated.

In the present specification, the device of the invention has been described with reference to a specific example shown in the drawing figures. It is to be noted, however, that the embodiment shown is only an example, and that other embodiments and variants of the invention are possible within the scope of the appended claims.

Furthermore, it is to be noted that although the invention has been described in detail with reference to the most preferred embodiment, i.e. a method and device for the administration of parenteral injections from an injection cartridge, this is not the only possible application of the invention. It is also possible to employ the method and device of the invention for the administration of pharmaceutical agents by other routes of administration than parenteral injections, such as intranasally, intraocularly, topically, rectally and otitic administration. The injection needle will then be replaced by some other administering means, and other modifications of the device may be necessary, as is apparent to those skilled in the art.

We claim:

1. A method for the repeated dosing of a liquid preparation of a pharmaceutically active agent to provide doses of a desired magnitude, by administration from a multi-dose container having a defined volume, said container having a fixed front wall through which is arranged an outlet for said preparation and a rear movable wall acting as a piston for expelling said preparation through said outlet by means of the movement of a piston rod connected to a dosing mechanism, and comprising the steps of:

a) defining a dose level of the pharmaceutically active agent adapted for unchanged but repeated administration to a patient;

b) selecting combination of (i) a concentration of the pharmaceutically active agent in the liquid preparation contained in the multi-dose container and (ii) a partial volume of said liquid preparation, which partial volume is 1/N of said defined volume of the multi-dose container, N being an integer having a value of 2 or higher, the combination of (i) and (ii) giving the dose level defined under a);

c) connecting a multi-dose container, containing the defined volume of liquid preparation of said concentration, to the piston rod and dosing mechanism; and d) performing exactly N individual and successive administration strokes with the piston rod, each stroke affecting the rear movable wall to expel an equal volume of the liquid preparation in each stroke, said volume being said partial volume; whereby the container is emptied after the N successive administration strokes.

2. A method according to claim 1, characterized in that said multi-dose container is an injection cartridge for parenteral injection.

3. A method according to claim 2, characterized in that the concentration of said liquid preparation in said multi-dose container is adapted to provide the desired dose.

4. A method according to claim 2, characterized in that N is an integer between 2 and 42.

5. A method according to claim 4, characterized in that the concentration of said liquid preparation in said multi-dose container is adapted to provide the desired dose.

6. A method according to claim 1, characterized in that the concentration of said liquid preparation in said multi-dose container is adapted to provide the desired dose.

7. A method according to claim 1, wherein the pharmaceutically active agent comprises growth hormones.

8. A device for repeated dosing of a liquid preparation of a pharmaceutically active agent, comprising a holder device for a multi-dose container having a defined volume and containing a preparation having a defined composition, said container having a fixed front wall through which is arranged an outlet for the preparation and a rear movable wall acting as a piston for expelling said preparation through said outlet, and a piston rod, by which the rear movable wall may be urged forwards, wherein the improvement comprises:

a) a movable chuck adapted to clamp around the piston rod under the action of a spring force, said clamping action being releasable by reducing said spring force;

b) jaws in said movable chuck having inclined surfaces and cooperating with locking means for closing the jaws and gripping the piston rod;

c) a yoke arrangement by means of which said movable chuck may be released and moved rearward along said piston rod; and d) at least one wall limiting the motion of said movable chuck, the wall being displaceable for setting the dose.

9. A device according to claim 8, characterized in that said blocking means, after the piston rod and the rear movable wall have been moved forward for said defined length, may be released from said piston rod and again be attached to it in such a position that said piston rod and said rear movable wall may again be moved forwards the same defined length, and this process may be repeated successively until the piston rod and the rear movable wall have been moved forwards N times, so that said multi-dose container is empty.

10. A device according to claim 9, characterized in that it is arranged as an injection device for repeated parenteral injections from an injection cartridge.

11. A device according to claim 8, characterized in that it is arranged as an injection device for repeated parenteral injections from an injection cartridge.

12. A device according to claim 11, characterized in that it comprises a barrel for holding at its front end an injection cartridge and a piston rod for actuating said injection cartridge for expelling a set amount of an injectable preparation from said cartridge, characterized in that said releasable blocking means comprise a fixed chuck and a movable chuck which clamp around the piston rod under the action of a spring force, said clamping action being releasable by reducing said spring force, and that said device further comprises a yoke arrangement, by means of which said movable chuck may be released and moved rearward along said piston rod, while at the same time cocking a spring when said movable chuck is again clamped around the piston rod, and means for releasing said fixed chuck, whereby said movable chuck and said piston rod may be moved forward by the action of said cocked spring, the distance that said movable chuck moves forward determining the magnitude of the dose set.

13. A device according to claim 12, characterized in that said injection cartridge is of the single-chamber type.

14. A device according to claim 12, characterized in that said injection cartridge is of the dual-chamber type.

15. A device according to claim 11, characterized in that said injection cartridge is of the single-chamber type.

16. A device according to claim 11, characterized in that said injection cartridge is of the dual-chamber type.

\* \* \* \* \*